United States Patent
Ichiyanagi et al.

(10) Patent No.: US 11,208,675 B2
(45) Date of Patent: Dec. 28, 2021

(54) REACTION ACCELERATING AGENT

(71) Applicant: Kikkoman Corporation, Noda (JP)

(72) Inventors: Atsushi Ichiyanagi, Chiba (JP);
Kazuhiko Shimoji, Chiba (JP)

(73) Assignee: Kikkoman Corporation, Chiba (JP)

( * ) Notice: Subject to any disclaimer, the term of this patent is extended or adjusted under 35 U.S.C. 154(b) by 104 days.

(21) Appl. No.: 16/317,209

(22) PCT Filed: Jul. 13, 2017

(86) PCT No.: PCT/JP2017/025621
§ 371 (c)(1),
(2) Date: Jan. 11, 2019

(87) PCT Pub. No.: WO2018/012606
PCT Pub. Date: Jan. 18, 2018

(65) Prior Publication Data
US 2019/0300929 A1  Oct. 3, 2019

(30) Foreign Application Priority Data

Jul. 13, 2016  (JP) .............................. JP2016-138640

(51) Int. Cl.
| C12Q 1/28 | (2006.01) |
| C09B 29/02 | (2006.01) |
| C09B 29/08 | (2006.01) |
| C09B 31/02 | (2006.01) |

(52) U.S. Cl.
CPC ............... *C12Q 1/28* (2013.01); *C09B 29/02* (2013.01); *C09B 29/0802* (2013.01); *C09B 29/0803* (2013.01); *C09B 31/025* (2013.01)

(58) Field of Classification Search
None
See application file for complete search history.

(56) References Cited

U.S. PATENT DOCUMENTS

| 4,855,228 A | 8/1989 | Charlton et al. |
| 5,445,755 A | 8/1995 | Convents et al. |
| 6,100,080 A | 8/2000 | Johansen |
| 2010/0112622 A1 | 5/2010 | Yonehara et al. |

FOREIGN PATENT DOCUMENTS

| JP | 01-109261 A | 4/1989 |
| JP | 08-503371 A | 4/1996 |
| JP | 10-501276 A | 2/1998 |
| JP | 2001-009466 A | 1/2001 |
| JP | 2001-508677 A | 7/2001 |
| WO | WO 94/12620 A1 | 6/1994 |
| WO | WO 2008/093722 A1 | 8/2008 |

OTHER PUBLICATIONS

Stiborova, M. et al., Collect. Czech Chem Comm. 1996, vol. 61, pp. 962-972.*
Morita, M. et al., Textile Res. 1996, vol. 66, pp. 470-473.*
International Search Report dated Oct. 10, 2017, in PCT/JP2017/025621.
Fujiyama et al., "Structure of horseradish peroxidase isozyme C genes," Eur. J. Biochem., 1988, 173:681-687.
Lin et al., "Functional Expression of Horseradish Peroxidase in *E. coli* by Directed Evolution," Biotechnol. Prog. 1999, 15:467-471.
Morawski et al., "Functional expression of horseradish peroxidase in *Saccharomyces cerevisiae* and *Pichia pastoris*," Protein Engineering, 2000, 13(5):377-384.
Sabnis et al., "Indicator Reagents," Ullmann's Encyclopedia of Industrial Chemistry, 2012,19:9-53.

* cited by examiner

*Primary Examiner* — Heidi Reese
(74) *Attorney, Agent, or Firm* — Foley & Lardner LLP

(57) ABSTRACT

Provided is a compound capable of accelerating the enzymatic reaction catalyzed by peroxidase. The present invention provides a peroxidase reaction accelerating agent comprising a compound represented by formula (I) and a method for measuring hydrogen peroxide using the same.

4 Claims, 1 Drawing Sheet

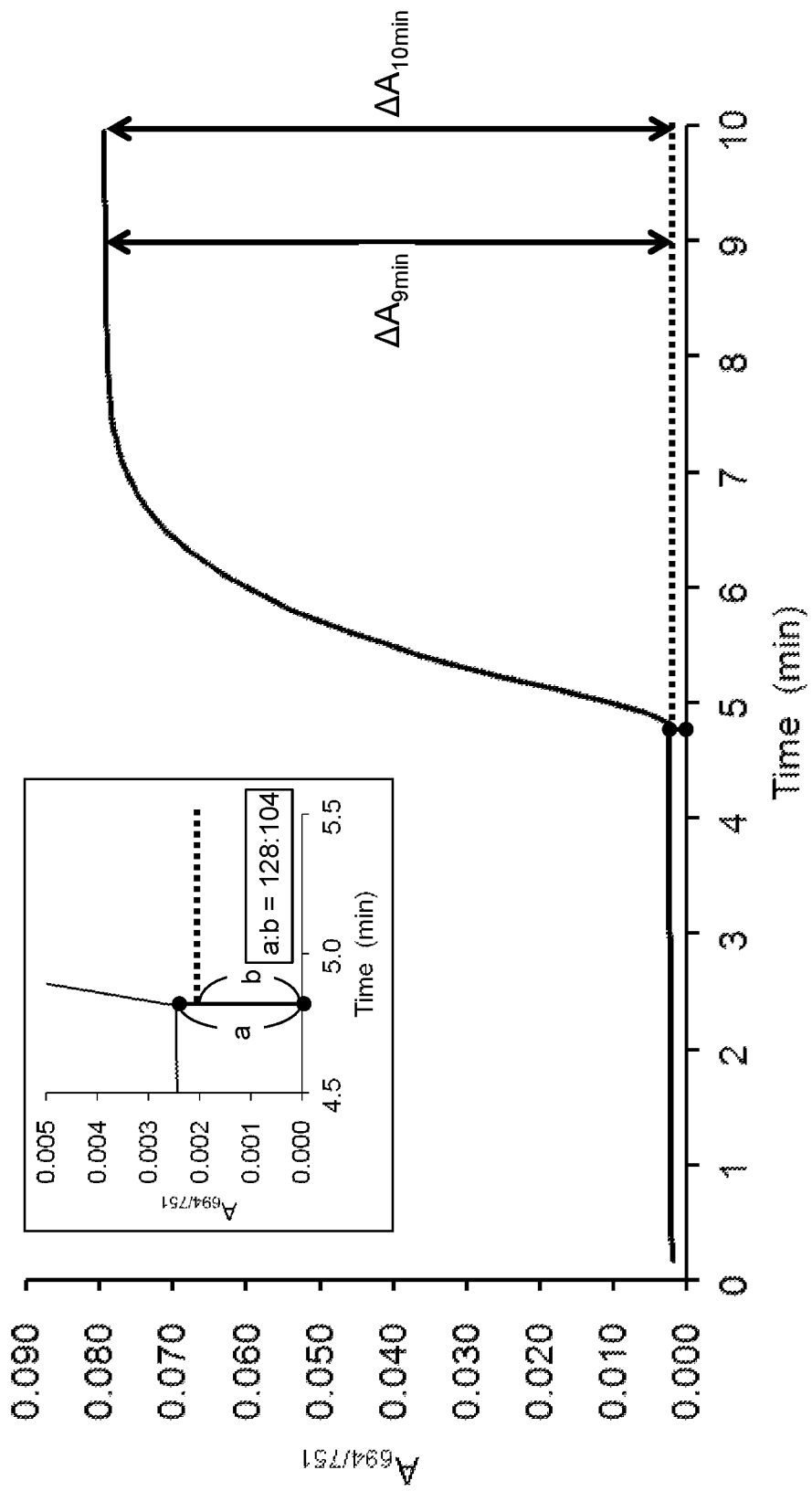

REACTION ACCELERATING AGENT

CROSS-REFERENCE TO RELATED APPLICATIONS

This application is the U.S. National Stage of PCT/JP2017/025621, filed Jul. 13, 2017, which claims priority to JP 2016-138640, filed Jul. 13, 2016.

TECHNICAL FIELD

The present invention relates to a reaction accelerating agent, for example, a reaction accelerating agent for peroxidase.

BACKGROUND ART

Peroxidase is widely utilized in various enzymatic measurement methods. For example, horseradish peroxidase (HRP) (EC1.11.1.7) is widely utilized in enzyme-linked immunosorbent assay (ELISA), various diagnostic kits, diagnostic drugs, detection reactions, and the like. However, supply of HRP depends mainly on natural raw materials and is obtained by harvesting cultivated *Armoracia rusticana*, followed by extraction and subsequent purification. As such, the yield of HRP is readily influenced by weather factors such as drought or change in temperature. Therefore, it is desirable to effectively utilize limited HRP resources.

Examples of the approach to this problem include a method for producing peroxidase by use of genetic recombination techniques in order to stabilize the yield of peroxidase. For example, the nucleotide sequence of a gene of typical peroxidase C1a and its amino acid sequence have been elucidated (Non Patent Literature 1). Although there have been attempts of recombinant expression using the C1a gene in *E. coli*, the expression level thereof is not high and is approximately 0.11 mg/L medium (Non Patent Literature 2). Further, the recombinant expression level in yeast is reported as approximately 5.3 mg/L (Non Patent Literature 3). However, in this expression system, sugar chains are added to the HRP and the sugar chain may influence antibody labeling when used in ELISA. Therefore, recombinantly expressed products have failed to replace natural raw materials. Further, even in the case of recombinant expression, the amount of peroxidase consumption is large and, there is a need for a method for effectively utilizing peroxidases.

Patent Literature 1 describes a compound shifting a detection wavelength of a phenothiazine derivative in a method for detecting a phenothiazine derivative dye in a reaction system by absorbance measurement.

CITATION LIST

Patent Literature

Patent Literature 1: International Publication No. WO 2008/093722

Non Patent Literature

Non Patent Literature 1: Eur. J. Biochem., 1988, vol. 173, pp. 681-687
Non Patent Literature 2: Biotechnol. Prog., 1999, vol. 15, pp. 467-471
Non Patent Literature 3: Protein. Engineering, 2000, vol. 13, pp. 377-384

SUMMARY OF INVENTION

Technical Problem

In light of the problems as mentioned above, the present invention provides a compound capable of accelerating enzymatic reaction catalyzed by peroxidase, i.e., a peroxidase reaction accelerating agent. The present invention further provides a composition comprising the peroxidase reaction accelerating agent. The present invention further provides a method for measuring hydrogen peroxide using peroxidase and a peroxidase reaction accelerating agent.

Solution to Problem

In order to solve the problems described above, the present inventors have carried out extensive studies and, as a result, surprisingly found a compound capable of accelerating the reaction of peroxidase, thereby completing the present invention. That is, the present invention encompasses the following embodiments.

[1] A method for measuring hydrogen peroxide, comprising the step of using peroxidase and a peroxidase reaction accelerating agent represented by the following formula (I):

[Formula 1]

$$R^1-N=N-R^2 \qquad (I)$$

wherein
$R^1$ and $R^2$ are each independently an aromatic 6-membered monocyclic carbocyclic ring, or a 10-membered fused ring containing the carbocyclic ring, wherein the ring may optionally be substituted with one or more substituents, wherein
the substituent(s) is selected from the group consisting of —F, —Cl, —Br, —I, —At, —$C_{1-6}$ alkyl, —$C_{2-6}$ alkenyl, —$C_{2-6}$ alkynyl, =O, —OH, —O—$C_{1-6}$ alkyl, —$CONH_2$, —$NO_2$, —$NH_2$, —CO—$NH_2$, —$R^3$, —NHCO—NH—$R^5$—N=N—$R^6$, —$SO_3X$, —COOX, Y, and Z;
X is selected from the group consisting of —H, —Na, —K, and —Li;
Y is selected from the group consisting of —H, —$SO_3X$, and —COOX;
Z is selected from the group consisting of —H, —$C_{1-6}$ alkyl, —O—$C_{1-6}$ alkyl, and —$SO_3X$;
—$R^3$ is —H or —NHCO—NH—$R^5$—N=N—$R^6$, or is an aromatic 6-membered monocyclic carbocyclic ring, or a 10-membered fused ring containing the carbocyclic ring, wherein the ring may optionally be substituted with one or more substituents selected from the group consisting of —F, —Cl, —Br, —I, —At, —$C_{1-6}$ alkyl, —$C_{2-6}$ alkenyl, —$C_{2-6}$ alkynyl, =O, —OH, —O—$C_{1-6}$ alkyl, —$CONH_2$, —$NO_2$, —$NH_2$, and —$SO_3X$; and
—$R^5$ and —$R^6$ are each independently an aromatic 6-membered monocyclic carbocyclic ring, or a 10-membered fused ring containing the carbocyclic ring, wherein the ring may optionally be substituted with one or more substituents selected from the group consisting of —F, —Cl, —Br, —I, —At, —$C_{1-6}$ alkyl, —$C_{2-6}$ alkenyl, —$C_{2-6}$ alkynyl, =O, —OH, —O—$C_{1-6}$ alkyl, —O—$CH_3$, —$CONH_2$, —$NO_2$, —$NH_2$, —$SO_3X$, —COOX, Y, and Z.

[2] The method according to 1, wherein regarding the peroxidase reaction accelerating agent represented by formula (I), $R^1$ and $R^2$ are each independently selected from the group consisting of

[Formula 2]
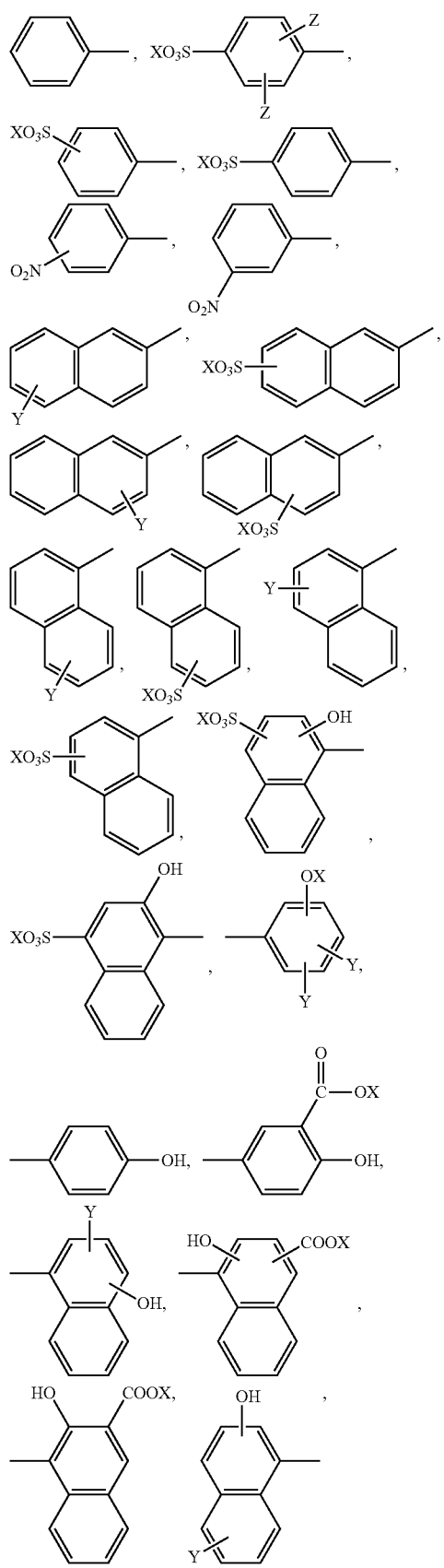
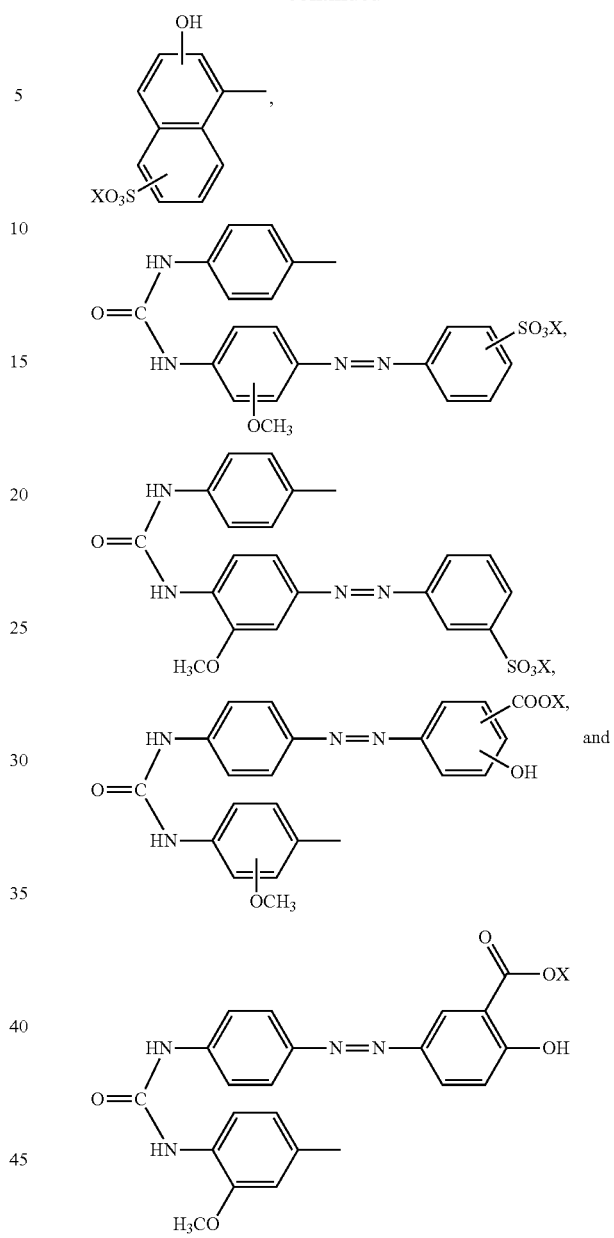
wherein X, Y, and Z are as defined in 1.
[3] The method according to 1 or 2, wherein regarding the peroxidase reaction accelerating agent represented by formula (I), $R^1$ is selected from the group consisting of
[Formula 3]
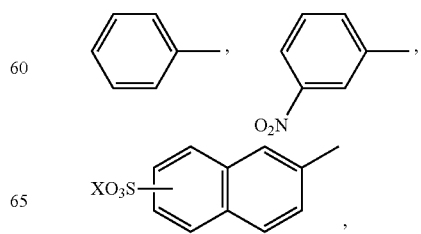

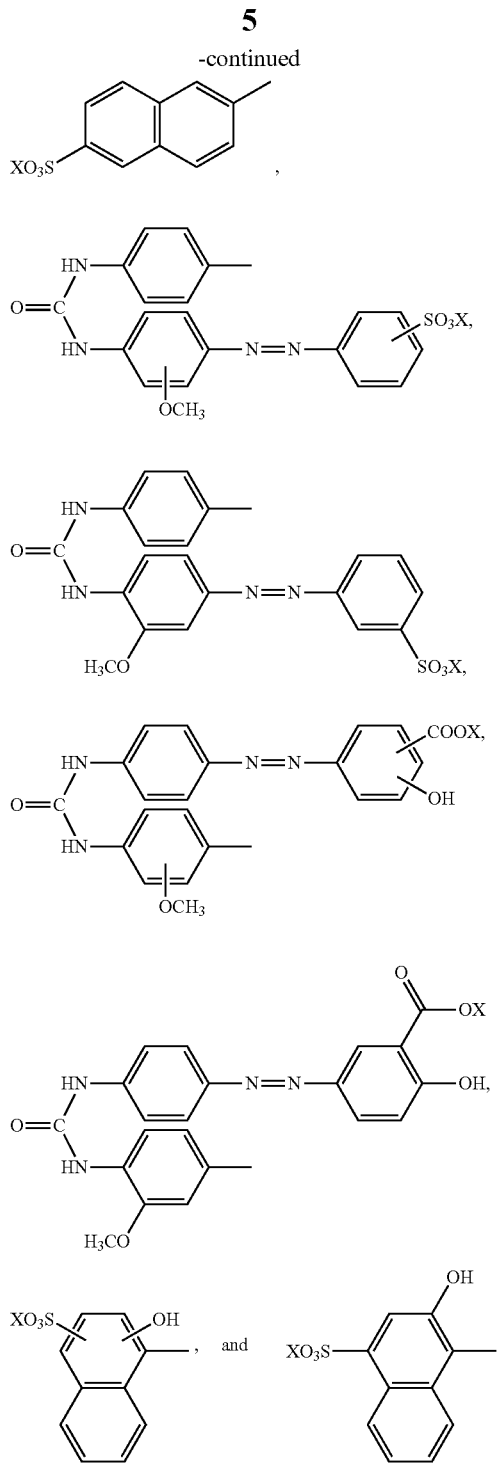

and R² is selected from the group consisting of

[Formula 4]

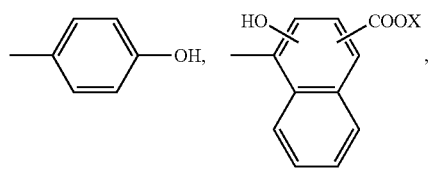

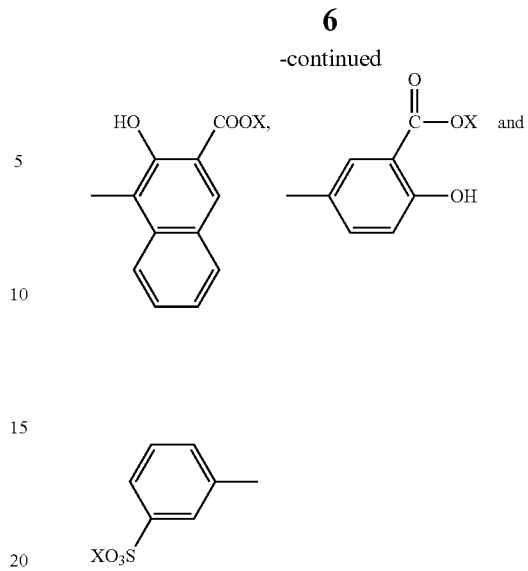

wherein X is as defined in 1.

[4] The method according to 1, wherein the peroxidase reaction accelerating agent represented by formula (I) is a peroxidase reaction accelerating agent represented by the following formula:

[Formula 5]

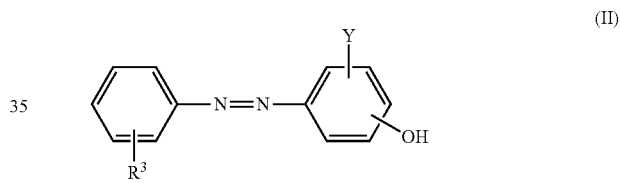

(II)

wherein

X is selected from the group consisting of —H, —Na, —K, and —Li;

Y is selected from the group consisting of —H, —SO₃X, and —COOX;

—R³ is —H or —NHCO—NH—R⁵—N=N—R⁶, or is an aromatic 6-membered monocyclic carbocyclic ring, or a 10-membered fused ring containing the carbocyclic ring, wherein the ring may optionally be substituted with one or more substituents selected from the group consisting of —F, —Cl, —Br, —I, —At, —C₁₋₆ alkyl, —C₂₋₆ alkenyl, —C₂₋₆ alkynyl, =O, —OH, —O—C₁₋₆ alkyl, —CONH₂, —NO₂, —NH₂, and —SO₃X; and —R⁵ and —R⁶ are each independently an aromatic 6-membered monocyclic carbocyclic ring, or a 10-membered fused ring containing the carbocyclic ring, wherein the ring may optionally be substituted with one or more substituents selected from the group consisting of —F, —Cl, —Br, —I, —At, —C₁₋₆ alkyl, —C₂₋₆ alkenyl, —C₂₋₆ alkynyl, =O, —OH, —O—C₁₋₆ alkyl, —O—CH₃, —CONH₂, —NO₂, —NH₂, and —SO₃X.

[5] The method according to 1, wherein the peroxidase reaction accelerating agent represented by formula (I) is a peroxidase reaction accelerating agent represented by any of the following formulae:

[Formula 6]

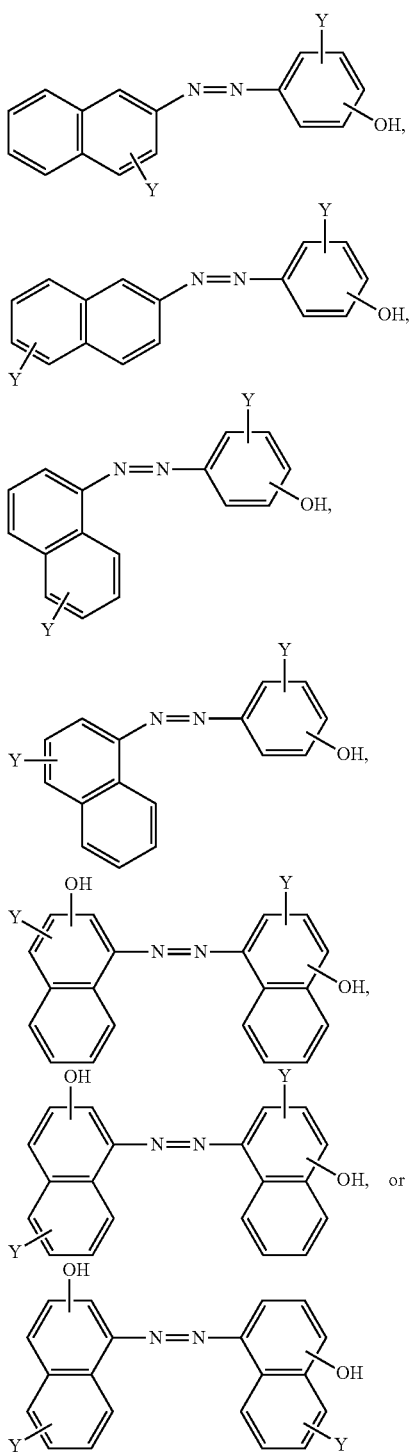

wherein
each X is independently selected from the group consisting of —H, —Na, —K, and —Li; and
each Y is independently selected from the group consisting of —H, —SO₃X, and —COOX.

[6] The method according to 1, wherein the peroxidase reaction accelerating agent represented by formula (I) is a peroxidase reaction accelerating agent represented by the following formula:

[Formula 7]

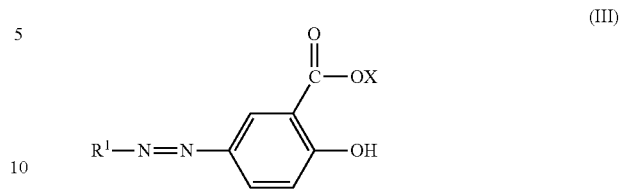

(III)

wherein $R^1$ is a benzene ring or a naphthalene ring which may optionally be substituted with one or more substituents, wherein the substituent(s) is selected from the group consisting of —NO₂, —SO₃X, and

[Formula 8]

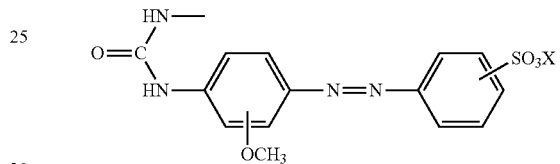

and

X is selected from the group consisting of —H, —Na, —K, and —Li.

[7] The method according to any of 1 to 6, wherein the compound represented by formula (I) is a compound selected from the group consisting of a compound represented by the following formula (4-(phenylazo)phenol, CAS 1689-82-3):

[Formula 9]

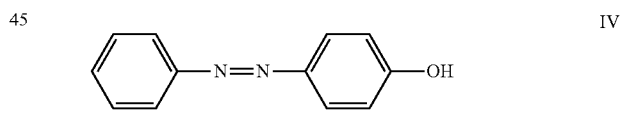

IV a compound represented by the following formula:

[Formula 10]

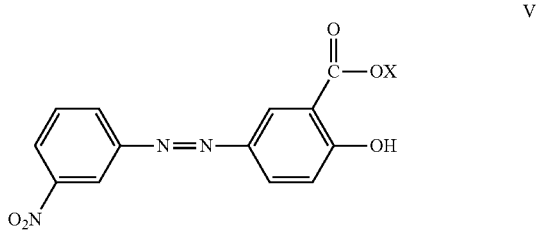

V wherein X is selected from the group consisting of —H, —Na, —K, and —Li, a compound represented by the following formula:

[Formula 11]

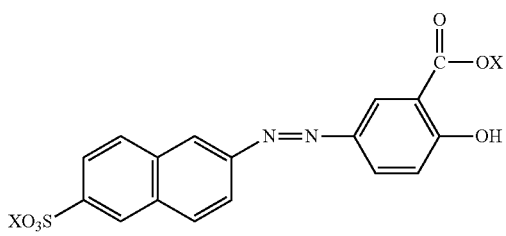
VI wherein each X is independently selected from the group consisting of —H, —Na, —K, and —Li,
a compound represented by the following formula:

[Formula 12]

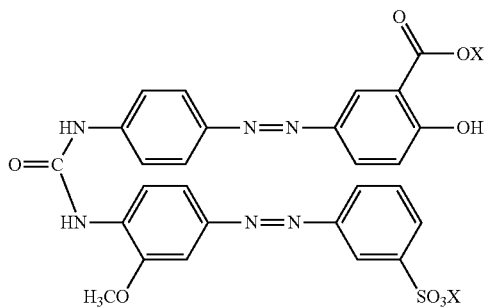
VII wherein each X is independently selected from the group consisting of —H, —Na, —K, and —Li,
and
a compound represented by the following formula:

[Formula 13]

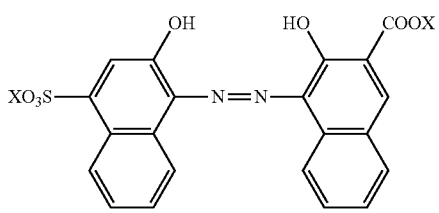
VIII wherein each X is independently selected from the group consisting of —H, —Na, —K, and —Li.

[8] A peroxidase reaction accelerating agent comprising a compound represented by formula (I):

[Formula 14]

 (I)

wherein
$R^1$ and $R^2$ are each independently an aromatic 6-membered monocyclic carbocyclic ring, or a 10-membered fused ring containing the carbocyclic ring, wherein the ring may optionally be substituted with one or more substituents, wherein the substituent(s) is selected from the group consisting of —F, —Cl, —Br, —I, —At, —$C_{1-6}$ alkyl, —$C_{2-6}$ alkenyl, —$C_{2-6}$ alkynyl, =O, —OH, —O—$C_{1-6}$ alkyl, —$CONH_2$, —$NO_2$, —$NH_2$, —CO—$NH_2$, —$R^3$, —NHCO—NH— $R^5$—N=N—$R^6$, —$SO_3X$, —COOX, Y, and Z;

X is selected from the group consisting of —H, —Na, —K, and —Li;

Y is selected from the group consisting of —H, —$SO_3X$, and —COOX;

Z is selected from the group consisting of —H, —$C_{1-6}$ alkyl, —O—$C_{1-6}$ alkyl, and —$SO_3X$;

—$R^3$ is —H or —NHCO—NH—$R^5$—N=N—$R^6$, or is an aromatic 6-membered monocyclic carbocyclic ring, or a 10-membered fused ring containing the carbocyclic ring, wherein the ring may optionally be substituted with one or more substituents selected from the group consisting of —F, —Cl, —Br, —I, —At, —$C_{1-6}$ alkyl, —$C_{2-6}$ alkenyl, —$C_{2-6}$ alkynyl, =O, —OH, —O—$C_{1-6}$ alkyl, —$CONH_2$, —$NO_2$, —$NH_2$, and —$SO_3X$; and —$R^5$ and —$R^6$ are each independently an aromatic 6-membered monocyclic carbocyclic ring, or a 10-membered fused ring containing the carbocyclic ring, wherein the ring may optionally be substituted with one or more substituents selected from the group consisting of —F, —Cl, —Br, —I, —At, —$C_{1-6}$ alkyl, —$C_{2-6}$ alkenyl, —$C_{2-6}$ alkynyl, =O, —OH, —O—$C_{1-6}$ alkyl, —O—$CH_3$, —$CONH_2$, —$NO_2$, —$NH_2$, —$SO_3X$, —COOX, Y, and Z.

[9] The peroxidase reaction accelerating agent according to 8, wherein regarding the compound represented by formula (I), $R^1$ and $R^2$ are each independently selected from the group consisting of

[Formula 15]

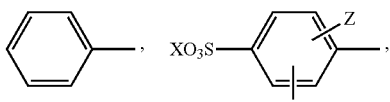

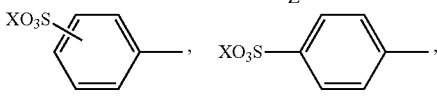

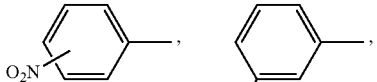

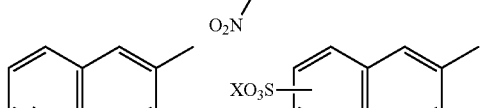

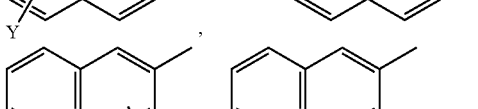

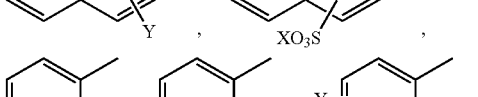

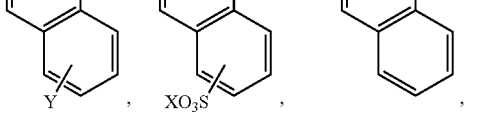

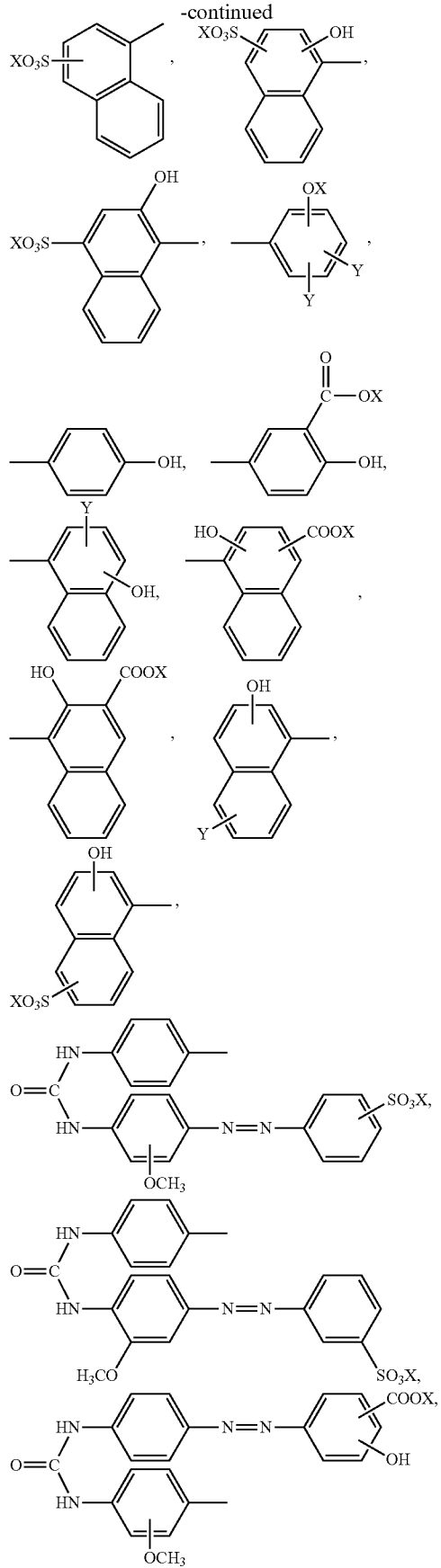
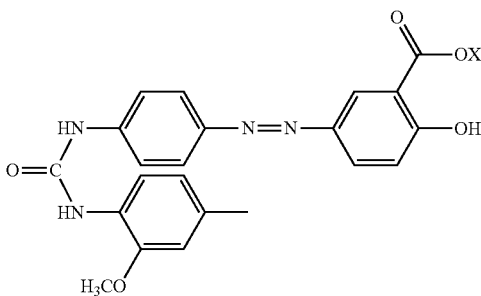
wherein X, Y, and Z are as defined in 8.
[10] The peroxidase reaction accelerating agent according to 8 or 9, wherein regarding the compound represented by formula (I), $R^1$ is selected from the group consisting of
[Formula 16]

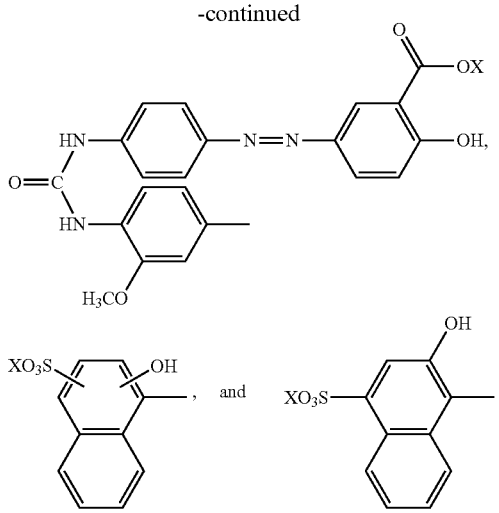

and R² is selected from the group consisting of

[Formula 17]

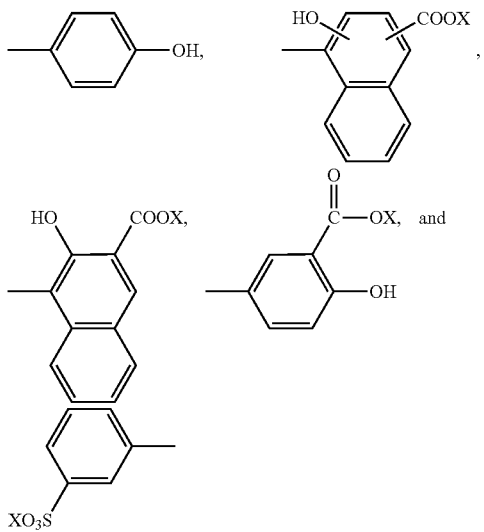

wherein X is as defined in 8.

[11] The peroxidase reaction accelerating agent according to 8, wherein the peroxidase reaction accelerating agent represented by formula (I) is a peroxidase reaction accelerating agent represented by the following formula:

[Formula 18]

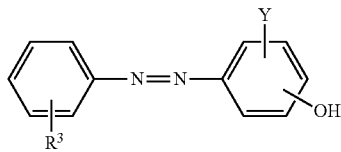
(II)

wherein
X is selected from the group consisting of —H, —Na, —K, and —Li;

Y is selected from the group consisting of —H, —SO₃X, and —COOX;

—R³ is —H or —NHCO—NH—R⁵—N=N—R⁶, or is an aromatic 6-membered monocyclic carbocyclic ring, or a 10-membered fused ring containing the carbocyclic ring, wherein the ring may optionally be substituted with one or more substituents selected from the group consisting of —F, —Cl, —Br, —I, —At, —C$_{1-6}$ alkyl, —C$_{2-6}$ alkenyl, —C$_{2-6}$ alkynyl, =O, —OH, —O—C$_{1-6}$ alkyl, —CONH₂, —NO₂, —NH₂, and —SO₃X; and —R⁵ and —R⁶ are each independently an aromatic 6-membered monocyclic carbocyclic ring, or a 10-membered fused ring containing the carbocyclic ring, wherein the ring may optionally be substituted with one or more substituents selected from the group consisting of —F, —Cl, —Br, —I, —At, —C$_{1-6}$ alkyl, —C$_{2-6}$ alkenyl, —C$_{2-6}$ alkynyl, =O, —OH, —O—C$_{1-6}$ alkyl, —O—CH₃, —CONH₂, —NO₂, —NH₂, and —SO₃X.

[12] The peroxidase reaction accelerating agent according to 8, wherein the peroxidase reaction accelerating agent represented by formula (I) is a peroxidase reaction accelerating agent represented by any of the following formulae:

[Formula 19]

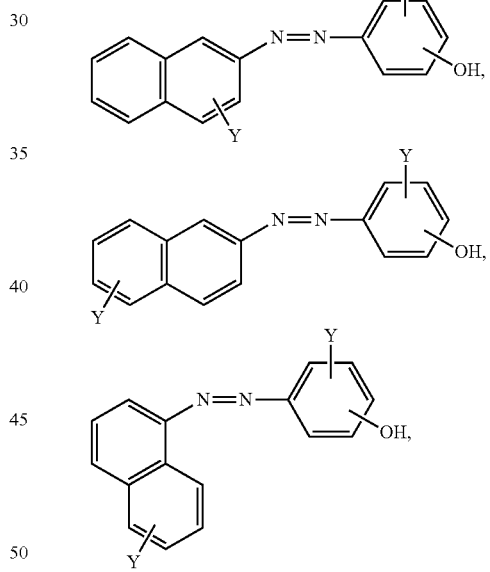

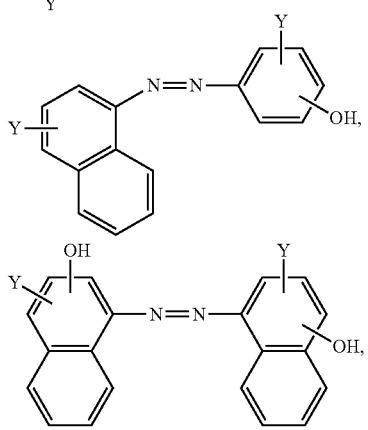

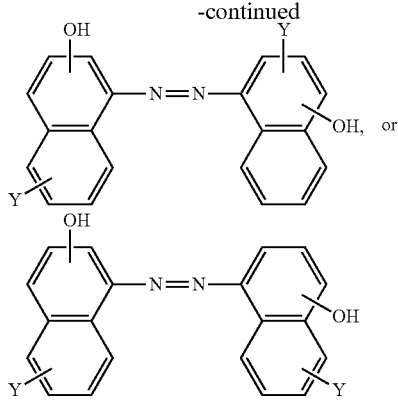

wherein each X is independently selected from the group consisting of —H, —Na, —K, and —Li; and each Y is independently selected from the group consisting of —H, —SO$_3$X, and —COOX.

[13] The peroxidase reaction accelerating agent according to 8, wherein the peroxidase reaction accelerating agent represented by formula (I) is a peroxidase reaction accelerating agent represented by the following formula:

[Formula 20]

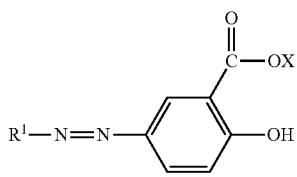

(III)

wherein

R$^1$ is a benzene ring or a naphthalene ring which may optionally be substituted with one or more substituents, wherein the substituent(s) is selected from the group consisting of —NO$_2$, —SO$_3$X, and

[Formula 21]

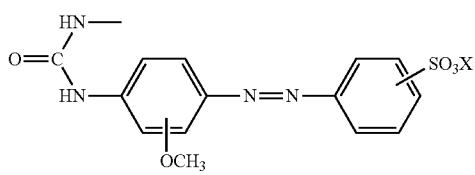

and

X is selected from the group consisting of —H, —Na, —K, and —Li.

[14] The peroxidase reaction accelerating agent according to any of 8 to 13, wherein the compound represented by formula (I) is a compound selected from the group consisting of a compound represented by the following formula (4-(phenylazo)phenol, CAS 1689-82-3):

[Formula 22]

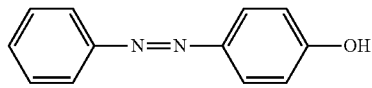

IV a compound represented by the following formula:

[Formula 23]

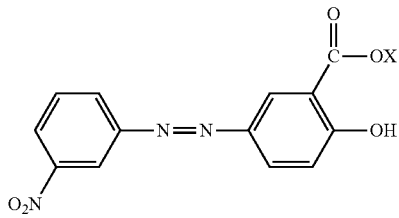

V wherein X is selected from the group consisting of —H, —Na, —K, and —Li, a compound represented by the following formula:

[Formula 24]

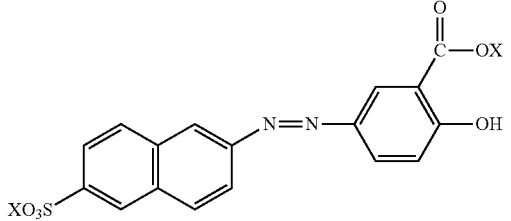

VI wherein each X is independently selected from the group consisting of —H, —Na, —K, and —Li, a compound represented by the following formula:

[Formula 25]

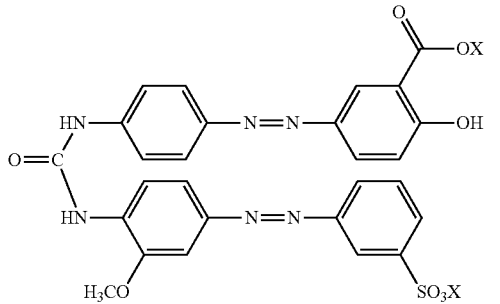

VII wherein each X is independently selected from the group consisting of —H, —Na, —K, and —Li,
and
a compound represented by the following formula:

[Formula 26]

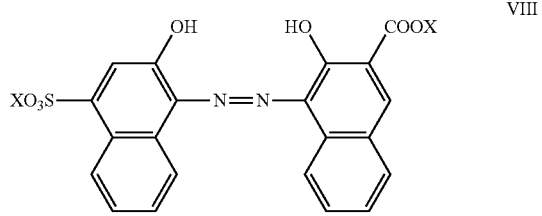

VIII wherein each X is independently selected from the group consisting of —H, —Na, —K, and —Li.

[15] A composition for hydrogen peroxide measurement comprising peroxidase and a peroxidase reaction accelerating agent according to any of 8 to 14.

[16] The composition according to 15, wherein the peroxidase is horseradish peroxidase.

The present specification encompasses the contents disclosed in Japanese Patent Application No. 2016-138640 on which the priority of the present application is based.

Advantageous Effects of the Invention

As an advantage (effect) of the present invention, the enzymatic reaction catalyzed by a peroxidase can be accelerated. This can lead to decrease in the amount of the peroxidase formulated into a diagnosis reagent or a measurement reagent, as compared with the case of not adding the peroxidase reaction accelerating agent of the present invention. If the same amount of peroxidase formulated, then since enzymatic reaction is accelerated, higher sensitivity of measurement and/or shortening of a reaction time can be achieved.

BRIEF DESCRIPTION OF DRAWING

FIG. 1 shows results of measuring the absorbance ($A_{694}$ and $A_{751}$) of a reaction solution for light at wavelengths of 694 nm and 751 nm over time for 10 minutes after mixing of a diluted sample with a first reagent-A. The abscissa depicts time (min), and the ordinate depicts $A_{694/751}$. The relationship between $A_{694/751}$ and $\Delta A_{9\ min}$ and $\Delta A_{10\ min}$ is also shown.

DESCRIPTION OF EMBODIMENTS

In one embodiment, the present invention provides a peroxidase reaction accelerating agent. The peroxidase reaction accelerating agent refers to a compound capable of accelerating (enhancing) the enzymatic reaction catalyzed by a peroxidase. The phrase "accelerating the enzymatic reaction catalyzed by a peroxidase" means that a larger amount of hydrogen peroxide is decomposed in the same reaction time, or the hydrogen peroxide degradation reaction is completed or almost completed in a shorter time, in the presence of the peroxidase reaction accelerating agent of the present invention in a system as compared to the absence of the peroxidase reaction accelerating agent in the system.

Any peroxidase known in the art can be used as the peroxidase. The peroxidase catalyzes the oxidation-reduction reaction between hydrogen peroxide and a color developing agent. The color developing agent develops color due to this reaction. In one embodiment, the peroxidase whose reaction is to be accelerated is horseradish peroxidase (HRP). In one embodiment, the peroxidase whose reaction is to be accelerated is hem-dependent peroxidase, for example, animal hem-dependent peroxidase, non-hem-dependent peroxidase, haloperoxidase, for example, lactoperoxidase, thiol peroxidase, for example, glutathione peroxidase, thyroid peroxidase, vanadium bromoperoxidase, or chloride peroxidase, ascorbate peroxidase, myeloperoxidase, lignin peroxidase, soybean peroxidase, *Arthromyces ramosus*-derived peroxidase, or *Coprinus*-derived peroxidase. The reaction accelerating agent of the present invention means a peroxidase reaction accelerating agent unless otherwise specified.

In one embodiment, the present invention provides a measurement method utilizing degradation of hydrogen peroxide, said method comprising the step of using peroxidase and a peroxidase reaction accelerating agent. In one embodiment, the measurement method of the present invention comprises the steps of: adding a first reagent containing the peroxidase and the peroxidase reaction accelerating agent to a sample containing hydrogen peroxide or a sample capable of producing hydrogen peroxide through enzymatic reaction or the like, followed by warming; adding thereto a second reagent containing a color developing agent, followed by warming; and measuring the absorbance of the sample. The first reagent containing the peroxidase and the peroxidase reaction accelerating agent may be a single reagent or may be a combination of a plurality of reagents containing the individual components (constituents) respectively. The second reagent containing a color developing agent may be a single reagent or may contain other components. The measurement may be qualitative or quantitative.

In another embodiment, the measurement method of the present invention comprises the steps of: adding a first reagent containing the peroxidase and a color developing agent to a second reagent containing the peroxidase reaction accelerating agent, followed by warming; and adding thereto a sample containing hydrogen peroxide or a sample capable of producing hydrogen peroxide through enzymatic reaction or the like, followed by warming. Again, each component in the reagent may be a single reagent or may be a combination of a plurality of reagents containing the individual components respectively.

The first reagent and the second reagent described above may be added as one reagent in a single step. That is, in an alternative embodiment, the measurement method of the present invention comprises the steps of: adding a measurement reagent containing the peroxidase, the peroxidase reaction accelerating agent, and a color developing agent to a sample which may contain hydrogen peroxide or a sample capable of producing hydrogen peroxide, followed by warming; and measuring the absorbance of the sample. The measurement reagent containing the peroxidase, the peroxidase reaction accelerating agent, and color developing agent may be a single reagent or may be a combination of a plurality of reagents containing the individual components respectively.

In one embodiment, horseradish peroxidase (HRP) can be used as the peroxidase. In this case, the measurement method of the present invention may further have a step for producing hydrogen peroxide serving as a substrate of HRP. Production of hydrogen peroxide can be performed through any reaction known in the art. For example, if hemoglobin A1c oxidase (A1cOX) capable of acting directly on HbA1c is added to a sample containing HbA1c, then HbA1c is oxidized and hydrogen peroxide is produced.

HRP may be free in a solution or may be immobilized on a solid phase. HRP may be used alone or may be linked to another compound or protein, for example, an enzyme or an antibody.

The final concentration of the reaction accelerating agent of the present invention added to the sample solution is not particularly limited and can be in the range of, for example, 0.01 to 200 mM, 0.02 to 150 mM, 0.03 to 100 mM, 0.04 to 80 mM, 0.05 to 60 mM, 0.06 to 50 mM, 0.08 to 40 mM, 0.1 mM to 30 mM, 0.15 to 20 mM, 0.2 to 10 mM, 0.3 to 5 mM, or 0.4 to 3 mM, for example, 0.05 to 10 mM. For example, when the concentration of hydrogen peroxide produced in the sample solution is 0 to 0.005 mM, the final concentration of the peroxidase reaction accelerating agent of the present invention added thereto can be, for example, 0.01 to 20 mM, for example, 0.02 to 10 mM. The final concentration of the reaction accelerating agent of the present invention added to the sample solution is not particularly limited and can be, for example, 0.001 to 5% (w/v), 0.003 to 3% (w/v), 0.005 to 1% (w/v), 0.01 to 0.5% (w/v), 0.02 to 0.3% (w/v), or 0.03 to 0.1% (w/v). The order of addition of the reaction accelerating agent, other enzymes, and reagents is not limited, and these components may be added concurrently or sequentially.

In one embodiment, the total reaction time can be 60 minutes or shorter, 30 minutes or shorter, or 20 minutes or shorter, preferably 15 minutes or shorter, preferably approximately 10 minutes. For example, the warming after the addition of the first reagent described above can be performed for 30 minutes or shorter, 20 minutes or shorter, 15 minutes or shorter, or 10 minutes, for example, approximately 5 minutes, and the warming after the addition of the second reagent described above can be performed for 30 minutes or shorter, 20 minutes or shorter, 15 minutes or shorter, or 10 minutes, for example, approximately 5 minutes. The concentration of each component in the measurement reagent with respect to the concentration range of hydrogen peroxide contained in the sample or presumably contained in the sample can be adjusted such that the reaction mediated by the peroxidase is completed or almost completed. The phrase "reaction is completed" means that the 100% of hydrogen peroxide contained in the sample, or hydrogen peroxide potentially producible from the sample has reacted. The phrase "reaction is almost completed" means that, for example, 75% or more, 80% or more, 85% or more, 90% or more, 95% or more, 96% or more, 97% or more, or 98% or more, for example, 99% or more, of hydrogen peroxide contained in the sample, or hydrogen peroxide potentially producible from the sample has reacted.

The measurement wavelength in the absorbance measurement can be selected depending on the color developing agent. The measurement wavelength of the absorbance can be, for example, 340 to 900 nm, 590 to 900 nm, 600 to 751 nm, or 610 to 730 nm. In one embodiment, the measurement may be performed at two measurement wavelengths $A_1$ and $A_2$, and the difference therebetween (also referred to as $A_1$-$A_2$ or $A_1/A_2$) can be obtained. The two measurement wavelengths $A_1$ and $A_2$ can be any two wavelengths in the range of 590 to 900 nm. For example, $A_1$ can be set to the absorption wavelength of a dye, and $A_2$ can be set to a background wavelength and then the difference therebetween ($A_1$-$A_2$) can be calculated. In the case of using a phenothiazine derivative dye, the measurement wavelength of the absorbance can be 590 to 730 nm, for example, 610 to 710 nm. In the case of using a phenothiazine derivative dye, the background wavelength can be selected from a region where the phenothiazine derivative dye is rarely absorbed, for example, the range of higher than 710 nm and 900 nm or lower. For example, when $A_1$ is $A_{694}$ and $A_2$ is $A_{751}$, $A_{694}$-$A_{751}$ may be calculated therefrom. The absorption wavelength may be set to $A_1$=$A_{654}$. The absorbance measurement may be performed using an automatic analysis apparatus.

The color developing agent is not particularly limited and may preferably be a compound that changes absorbance through the catalytic reaction of peroxidase in the presence of hydrogen peroxide. Examples of the color developing agent include 4-aminoantipyrine, ADOS (N-ethyl-N-(2-hydroxy-3-sulfopropyl)-m-anisidine), ALOS (N-ethyl-N-(2-hydroxy-3-sulfopropyl)aniline), TOOS (N-ethyl-N-(2-hydroxy-3-sulfopropyl)-m-toluidine sodium), DA-67 (10-(carboxymethylaminocarbonyl)-3,7-bis(dimethylamino)-phenothiazine), and DA-64 (N-(carboxymethylaminocarbonyl)-4,4'-bis(dimethylamino)-diphenyl amine). ADOS, ALOS, and TOOS develop color when condensed with 4-aminoantipyrine. DA-64 and DA-67 develop color by mere incorporation alone without the need of 4-aminoantipyrine. In any of the cases, the coloring reaction is catalyzed by peroxidase. Further examples of the color developing agent include, but are not limited to, methylene blue, 10-(acetylaminocarbonyl)-3,7-bis(dimethylamino) phenothiazine, 10-(carboxymethylaminocarbonyl)-3,7-bis (dimethyl amino)phenothiazine, 10-(phenyl carbonyl)-3,7-bis(dimethylamino)phenothiazine, 10-(3-(methylcarboxyamino)-hexamethyl-amino)-phenothiazine, 10-((3-(methylcarboxyamino)-4-methyl-phenyl)-amino)-phenothiazine, (methylcarboxyaminomethyl)-phenyl)-methylamino)-phenothiazine, 10-(1-naphthaleneamino)-phenothiazine, 10-(methyl)-phenothiazine, 10-(phenylamino)-phenothiazine, 10-(methylamino)-phenothiazine, azure A, azure B, azure C, toluidine blue 0, 1,9-dimethyl-3,7-bis(dimethylamino)phenothiazine salt, methylene green and salts thereof, and leuco forms thereof. The color developing agent can be added such that its final concentration in the reaction solution is 0.001 to 10 mM, for example, 0.005 to 2 mM.

Any peroxidase known in the art can be used as the peroxidase for use in the measurement reaction. In one embodiment, the peroxidase is horseradish peroxidase (HRP). In one embodiment, the peroxidase is hem-dependent peroxidase, for example, animal hem-dependent peroxidase, non-hem-dependent peroxidase, haloperoxidase, for example, lactoperoxidase (LPO), thiol peroxidase, for example, glutathione peroxidase (GluP), thyroid peroxidase (TPO), vanadium bromoperoxidase (VBrPO), or chloride peroxidase (ClPO). As these enzymes, those known in the art or commercially available products may be utilized.

Horseradish peroxidase (HRP) catalyzes the following reaction.

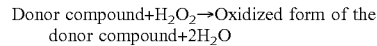
Donor compound+$H_2O_2$→Oxidized form of the donor compound+$2H_2O$

The donor compound may also be referred to as an electron donor. Examples thereof include phenol, guaiacol, and pyrogallol compounds and the like. While isozymes exist for HRP, in the present specification, HRP refers to peroxidase C1a, which is the principal isozyme. HRP comprises four intramolecular S—S bonds. Further, calcium ions are essential for the structural formation of HRP. Furthermore, HRP requires a hem cofactor for enzymatic activity thereof.

The hydrogen peroxide degradation reaction can be performed in a buffering solution. In the case of performing hydrogen peroxide production reaction as well, the same buffering solution as that for the production reaction can be used in the hydrogen peroxide degradation reaction. The pH of the reaction solution is not particularly limited and can be, for example, 3 to 11, 4 to 10, or 5 to 9, for example, 6 to 8. The reaction temperature can be, for example, 10 to 45° C., 10 to 40° C., 10 to 38° C., or 20 to 37° C., for example, 25 to 37° C. The reaction time can be 0.1 to 60 minutes, 0.1 to 30 minutes, 0.1 to 20 minutes, 0.1 to 15 minutes, or 0.1 to 10 minutes, for example, 0.1 to 5 minutes.

Although depending on the amount of hydrogen peroxide or substrate which may produce hydrogen peroxide contained in the sample solution, the peroxidase can be added at a final concentration of for example 0.01 to 300 KU/L, 0.01 to 100 KU/L, 0.01 to 50 U/mL, 0.1 to 20 U/mL, 0.2 to 10 U/mL, 0.5 to 50 KU/L, for example 0.5 to 10 U/mL, to the reaction solution. The activity "U" of the peroxidase is defined such that the amount of the enzyme (POD) producing 1 mg of purpurogallin in 20 seconds under the following reaction conditions is 1 purpurogallin unit:

Reagent:
A. 5% (W/V) pyrogallol aqueous solution
B. 0.147 M $H_2O_2$ solution (1.67 ml of a 30% (W/V) $H_2O_2$ solution is diluted to 100 ml with distilled water)
C. 0.1 M phosphate buffer solution, pH 6.0 (for reaction mixture and enzyme dilution)
D. 2.0 N $H_2SO_4$ solution Enzyme solution: an enzyme preparation is dissolved in a 0.1 M phosphate buffer solution, pH 6.0 cooled in ice in advance, and the solution is diluted to 3.0 to 6.0 purpurogallin U/P with the same buffer solution as above and preserved under ice cooling.

Procedures:
1 A reaction mixture of the components given below is prepared in a test tube (32ϕ×200 mm) and preliminarily warmed at 20° C. for approximately 5 minutes.
14.0 ml of distilled water
2.0 ml of an aqueous pyrogallol solution (A)
1.0 ml of an aqueous $H_2O_2$ solution (B)
2.0 ml of a phosphate buffer solution (C)
2 The reaction is started by the addition of 1.0 ml of an enzyme solution.
3 After reaction at 20° C. for precisely 20 seconds, the reaction is terminated by the addition of 1.0 ml of a $H_2SO_4$ solution (D). After the termination of the reaction, the produced purpurogallin is extracted from the mixture with 15 ml of ether. This operation is repeated 5 times, and the extracts are combined. Ether is further added thereto to adjust the whole amount to 100 ml. The absorbance of this solution is measured at 420 nm (OD test).
4 For a blind test, the reaction mixture 1 is left at 20° C. for 20 seconds. Then, 1.0 ml of the $H_2SO_4$ solution (D) is added thereto, followed by mixing. Subsequently, 1.0 ml of an enzyme solution is added thereto for preparation. This solution is subjected to ether extraction and absorbance measurement in the same manner as above (OD blank).
The calculation formula is as follows:

$$U/ml = \Delta OD(OD \text{ test} - OD \text{ blank}) \times \text{Dilution ratio}/(0.117 \times 1 \text{ ml})$$
$$= \Delta OD \times 8.547 \times \text{Dilution ratio}$$
$$U/mg = U/ml \times 1/C$$

0.117: absorbance of 1 mg % purpurogallin ether solution at 420 nm
C: enzyme concentration (c mg/ml) at the time of dissolution
1 purpurogallin unit corresponds to 13.5 international units (under reaction conditions of 25° C. with o-dianisidine as a substrate).

The absorbance measurement can be carried out with any spectrophotometer or detection instrument known in the art. The absorbance of the reaction solution indicates the amount of the color developing agent that has developed color and the hydrogen peroxide concentration in the sample can be determined therefrom. Further, the concentration of a substrate for producing hydrogen peroxide can be determined when the reaction of producing hydrogen peroxide is conjugated (coupled) therewith. The absorbance of a standard material containing hydrogen peroxide having a known concentration can be measured, and the relationship between the concentration and the absorbance can be plotted to prepare a calibration curve. Subsequently, the absorbance of a sample containing hydrogen peroxide having an unknown concentration, or a substrate for producing the hydrogen peroxide can be measured, and the concentration of the hydrogen peroxide, or the substrate for producing the hydrogen peroxide can be determined from the calibration curve.

In one embodiment, the present invention provides a composition for hydrogen peroxide measurement comprising a peroxidase reaction accelerating agent. This composition may optionally comprise an enzyme capable of producing hydrogen peroxide, peroxidase, a buffer, a stabilizer, a color developing agent, a surfactant and the like. An additional enzyme or reagent for measurement of a compound other than hydrogen peroxide may also be added to the composition of the present invention.

Examples of the buffer include N-[tris(hydroxymethyl)methyl]glycine, phosphate, acetate, carbonate, tris(hydroxymethyl)-aminomethane, borate, citrate, dimethylglutamate, Tricine, HEPES, MES, Bis-Tris, ADA, PIPES, ACES, MOPSO, BES, MOPS, TES, DIPSO, TAPSO, POPSO, HEPPSO, EPPS, Tricine, Bicine, TAPS, phthalic acid, and tartaric acid. The composition of the present invention may be appropriately further supplemented, if necessary, a solubilizer, a stabilizer, a reactivity improving agent, an HbA1c denaturant, or the like, such as a surfactant (n-octyl-β-D-glucoside, n-octyl-β-D-thioglucoside, n-dodecyl-ρ-D-maltoside, n-tetradecyl-β-D-maltoside, n-octyl-β-D-maltoside, 1-dodecylpyridinium salt, hexadecyl trimethylammonium salt, tetradecyl trimethylammonium salt, dodecyl trimethylammonium salt, Triton X-100, Bridge 35, Bridge 58, Tween 80, cholate, n-heptyl-3-D-thioglucoside, 3-oxatridecyl-α-D-mannoside, n-nonyl-β-D-thiomaltoside, n-decyl-β-D-maltoside, n-undecyl-β-D-maltoside, trehalose C8, trehalose C10, trehalose C12, trehalose C14, trehalose C16, BIGCHAP, deoxy-BIGCHAP, MEGA-8, MEGA-9, MEGA-10, hexadecylpyridinium salt, octadecyl trimethylammonium salt, decyl trimethylammonium salt, nonyl trimethylammonium salt, octyl trimethylammonium salt, hexyl trimethylammonium salt, sodium dodecyl sulfate, and the like), a reducing agent (dithiothreitol, mercaptoethanol, L-cysteine, and the like), nitrite, bovine serum albumin, or a saccharide (glycerin, lactose, sucrose, and the like).

In one embodiment, the peroxidase reaction accelerating agent of the present invention comprises a compound represented by the following formula (I):

[Formula 27]

  (I)

wherein
R¹ and R² are each independently an aromatic 6-membered monocyclic carbocyclic ring, or a 10-membered fused ring containing the carbocyclic ring, wherein the ring may optionally be substituted with one or more substituents, wherein
the substituent(s) is selected from the group consisting of —F, —Cl, —Br, —I, —At, —$C_{1-6}$ alkyl, —$C_{2-6}$ alkenyl, —$C_{2-6}$ alkynyl, =O, —OH, —O—$C_{1-6}$ alkyl, —CONH$_2$, —NO$_2$, —NH$_2$, —CO—NH$_2$, —R³, —NHCO—NH—R⁵—N=N—R⁶, —SO$_3$X, —COOX, Y, and Z;
X is selected from the group consisting of —H, —Na, —K, and —Li;
Y is selected from the group consisting of —H, —SO$_3$X, and —COOX;
Z is selected from the group consisting of —H, —$C_{1-6}$ alkyl, —O—$C_{1-6}$ alkyl, and —SO$_3$X;
—R³ is —H or —NHCO—NH—R⁵—N=N—R⁶, or is an aromatic 6-membered monocyclic carbocyclic ring, or a 10-membered fused ring containing the carbocyclic ring, wherein the ring may optionally be substituted with one or more substituents selected from the group consisting of —F, —Cl, —Br, —I, —At, —$C_{1-6}$ alkyl, —$C_{2-6}$ alkenyl, —$C_{2-6}$ alkynyl, =O, —OH, —O—$C_{1-6}$ alkyl, —CONH$_2$, —NO$_2$, —NH$_2$, and —SO$_3$X; and
—R⁵ and —R⁶ are each independently an aromatic 6-membered monocyclic carbocyclic ring, or a 10-membered fused ring containing the carbocyclic ring, wherein the ring may optionally be substituted with one or more substituents selected from the group consisting of —F, —Cl, —Br, —I, —At, —$C_{1-6}$ alkyl, —$C_{2-6}$ alkenyl, —$C_{2-6}$ alkynyl, =O, —OH, —O—$C_{1-6}$ alkyl, —O—CH$_3$, —CONH$_2$, —NO$_2$, —NH$_2$, —SO$_3$X, —COOX, Y, and Z.

The 6-membered monocyclic ring may optionally be substituted with 1, 2, 3, 4 or 5 substituents. The 10-membered fused ring may optionally be substituted with 1, 2, 3, 4, 5, 6 or 7 substituents.

Examples of the aromatic monocyclic carbocyclic ring include a benzene ring. Examples of the fused ring of an aromatic carbocyclic ring and carbocyclic ring include a naphthalene ring.

Examples of the —$C_{1-6}$ alkyl include methyl, ethyl, propyl (n-propyl, isopropyl), butyl (n-butyl, sec-butyl, isobutyl, tert-butyl), pentyl (n-pentyl, tert-pentyl, neopentyl, isopentyl, sec-pentyl, 3-pentyl), and hexyl (n-hexyl, isohexyl, neohexyl) groups.

Examples of the —$C_{2-6}$ alkenyl include an ethenyl group (vinyl group), a 1-propenyl group, a 2-propenyl group (allyl group), a 1-butenyl group, a 2-butenyl group, a 3-butenyl group, a pentenyl group, and a hexenyl group.

Examples of the —$C_{2-6}$ alkynyl include an ethynyl group, a 1-propynyl group, a 2-propynyl group, a 1-butynyl group, a 2-butynyl group, a 3-butynyl group, a pentynyl group, and a hexynyl group.

The —O—$C_{1-6}$ alkyl may also be referred to as a $C_{1-6}$ alkoxy group and examples thereof include linear or branched alkoxy groups such as methoxy, ethoxy, propoxy, butoxy, pentyloxy, and hexyloxy.

In one embodiment, R¹ and R² are each independently an aromatic 6-membered monocyclic carbocyclic ring (benzene ring) which may optionally be substituted with one or more substituents. In one embodiment, R¹ is an aromatic 6-membered monocyclic carbocyclic ring which may optionally be substituted with one or more substituents, and R² is a 10-membered carbocyclic fused ring (naphthalene ring).

In one embodiment, R¹ and R² are each independently a group selected from the group consisting of

[Formula 28]

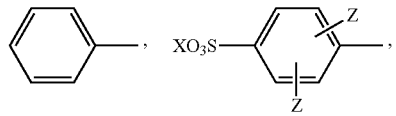

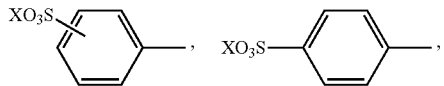

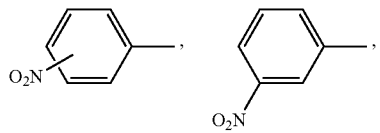

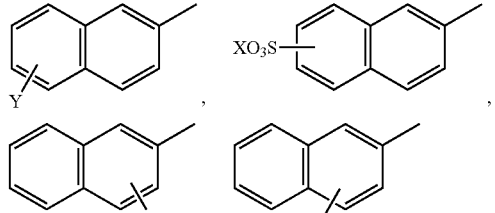

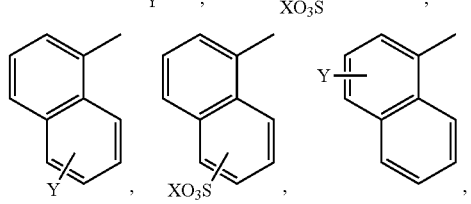

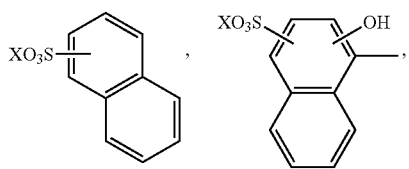

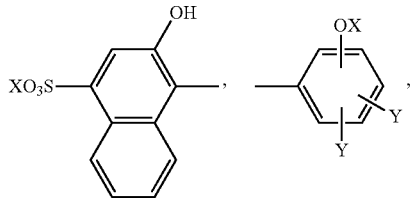

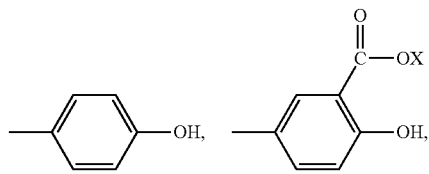

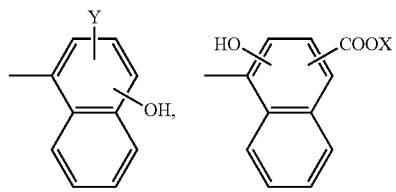

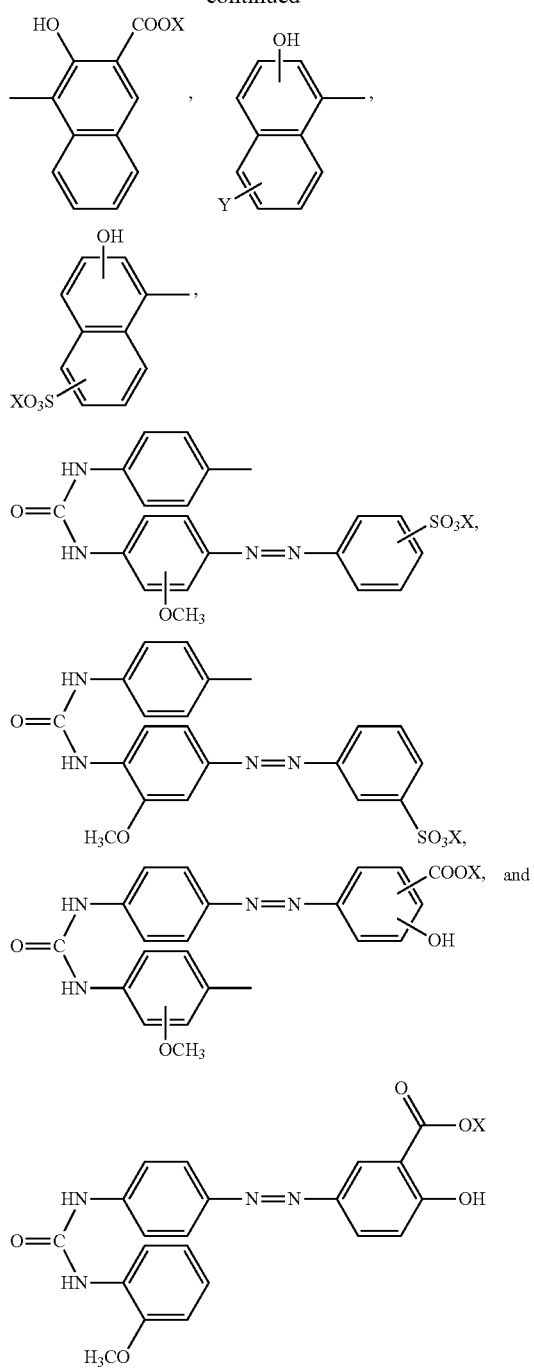
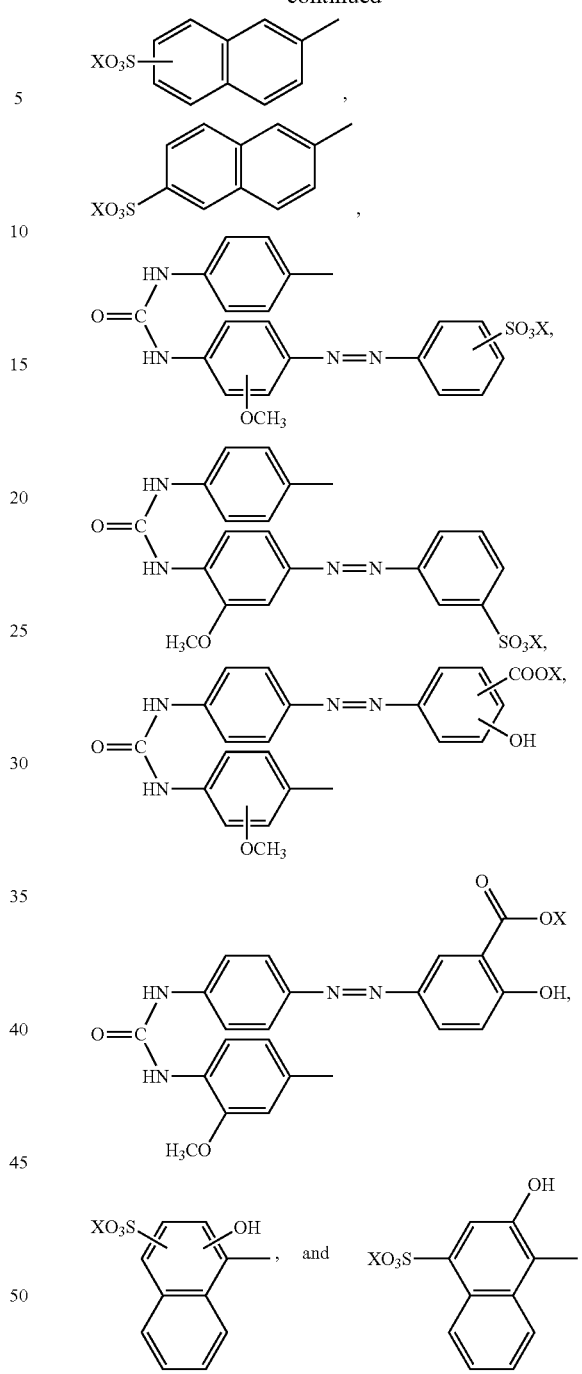
In the formulae, X, Y, and Z are as defined above.
In one embodiment, R[1] is selected from the group consisting of
[Formula 29]
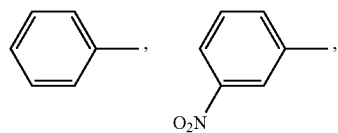
and R[2] is selected from the group consisting of
[Formula 30]
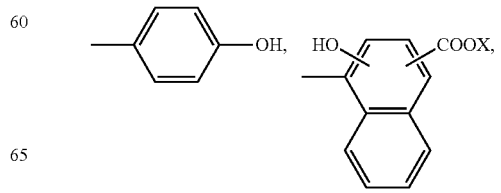

-continued

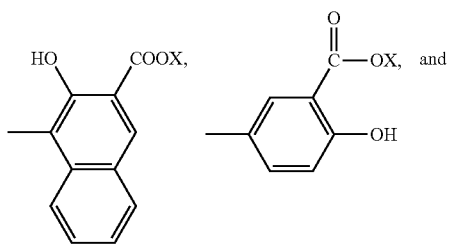

wherein X is as defined above.

In one embodiment, the peroxidase reaction accelerating agent of the present invention comprises a peroxidase reaction accelerating agent represented by the following formula:

[Formula 31]

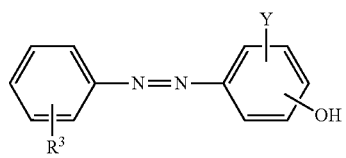

(II)

wherein

X is selected from the group consisting of —H, —Na, —K, and —Li;

Y is selected from the group consisting of —H, —SO₃X, and —COOX;

—R³ is —H or —NHCO—NH—R⁵—N=N—R⁶, or is an aromatic 6-membered monocyclic carbocyclic ring, or a 10-membered fused ring containing the carbocyclic ring, wherein the ring may optionally be substituted with one or more substituents selected from the group consisting of —F, —Cl, —Br, —I, —At, —C₁₋₆ alkyl, —C₂₋₆ alkenyl, —C₂₋₆ alkynyl, =O, —OH, —O—C₁₋₆ alkyl, —CONH₂, —NO₂, —NH₂, and —SO₃X; and —R⁵ and —R⁶ are each independently an aromatic 6-membered monocyclic carbocyclic ring, or a 10-membered fused ring containing the carbocyclic ring, wherein the ring may optionally be substituted with one or more substituents selected from the group consisting of —F, —Cl, —Br, —I, —At, —C₁₋₆ alkyl, —C₂₋₆ alkenyl, —C₂₋₆ alkynyl, =O, —OH, —O—C₁₋₆ alkyl, —O—CH₃, —CONH₂, —NO₂, —NH₂, and —SO₃X.

In one embodiment, the peroxidase reaction accelerating agent of the present invention comprises a peroxidase reaction accelerating agent represented by any of the following formulae:

[Formula 32]

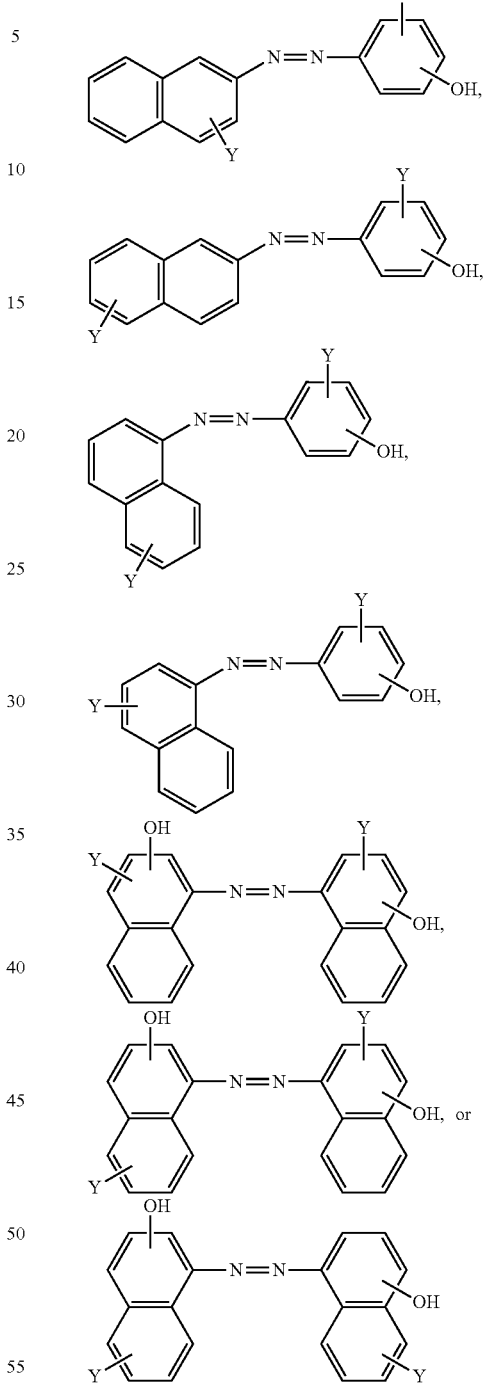

wherein each X is independently selected from the group consisting of —H, —Na, —K, and —Li; and each Y is independently selected from the group consisting of —H, —SO₃X, and —COOX.

In one embodiment, the peroxidase reaction accelerating agent of the present invention comprises a peroxidase reaction accelerating agent represented by the following formula:

[Formula 33]

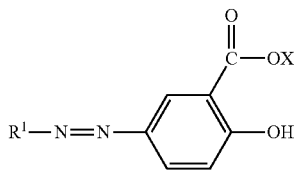

(III)

wherein

R¹ is a benzene ring or a naphthalene ring which may optionally be substituted with one or more substituents, wherein the substituent(s) is selected from the group consisting of —NO₂, —SO₃X, and

[Formula 34]

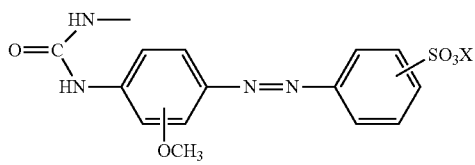

and

X is selected from the group consisting of –H, —Na, —K, and —Li.

In one embodiment, the peroxidase reaction accelerating agent of the present invention is a compound selected from the group consisting of a compound represented by the following formula (4-(phenylazo)phenol, CAS 1689-82-3):

[Formula 35]

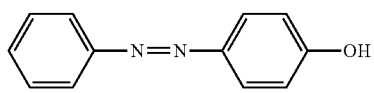

IV a compound represented by the following formula:

[Formula 36]

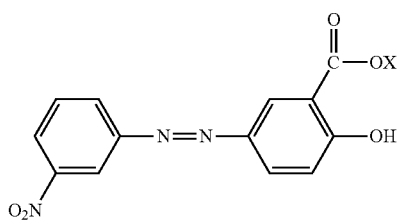

V wherein X is selected from the group consisting of —H, —Na, —K, and —Li, for example, the following Alizarin Yellow GG (CAS 584-42-9):

[Formula 37]

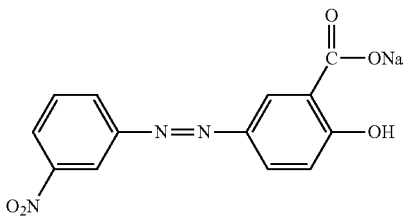

Alizarin Yelow GG a compound represented by the following formula:

[Formula 38]

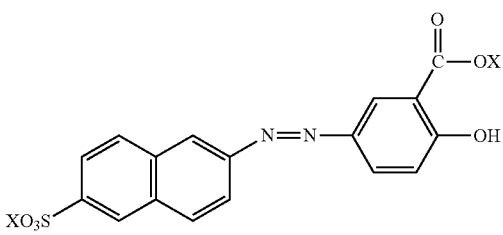

VI wherein each X is independently selected from the group consisting of —H, —Na, —K, and —Li, for example, the following Chrome Yellow (CAS 6054-97-3):

[Formula 39]

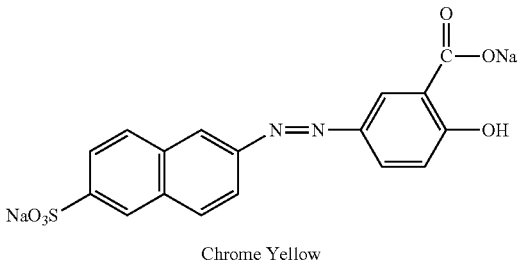

Chrome Yellow a compound represented by the following formula:

[Formula 40]

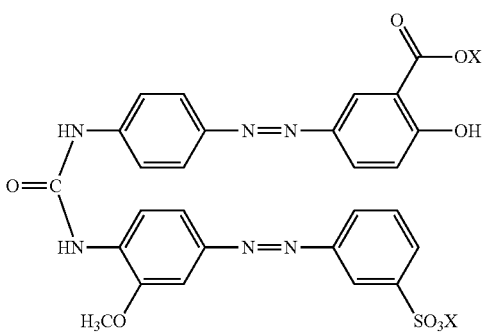

VII wherein each X is independently selected from the group consisting of —H, —Na, —K, and —Li, for example, the following Direct Yellow 44 (CAS 8005-52-5):

[Formula 41]

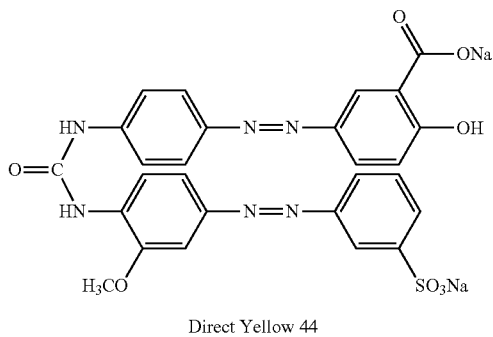

Direct Yellow 44 and
a compound represented by the following formula:

[Formula 42]

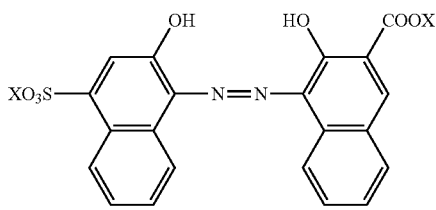

VIII wherein each X is independently selected from the group consisting of —H, —Na, —K, and —Li, for example, the following 2-hydroxy-1-(2-hydroxy-4-sulfo-1-naphthylazo)-3-naphthoic acid (CAS 3737-95-9):

[Formula 43]

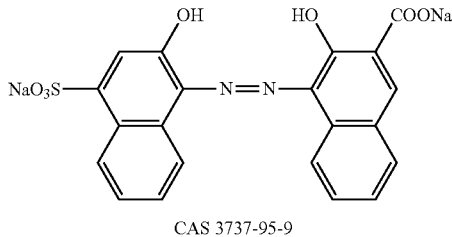

CAS 3737-95-9

The compound represented by the following formula (Tartrazine, C A S 1934-21-0) is excluded from the reaction accelerating agent of the present invention:

[Formula 44]

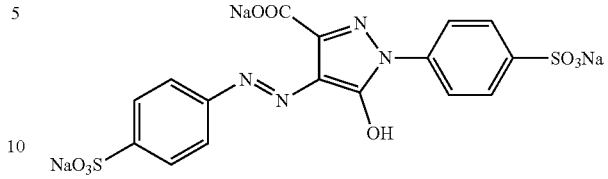

IX

As the compounds of formula IV to formula VIII, commercially available products, or salts thereof may be used. Other compounds of formulae I to III may be synthesized by routine approaches or commercially available products may be used.

Whether or not the compound accelerates hydrogen peroxide degradation reaction mediated by peroxidase can be evaluated by comparing the progression of the reaction by the addition of a candidate compound to the system with the progression of the reaction without the addition.

(Example of Hydrogen Peroxide Measurement Method)

Examples of the hydrogen peroxide measurement reagent and measurement method of the present invention will be described below. However, the present invention is not limited to these examples.

For hydrogen peroxide and the dye, commercially available products can be used. Peroxidase may be purified from a natural source, or a commercially available product may be used.

The following reagents for hydrogen peroxide measurement are prepared.

Hydrogen peroxide sample having a known concentration 0 to 0.0003% (w/v) hydrogen peroxide First reagent-A (solution containing peroxidase and leuco dye)

30 mM MOPS-NaOH buffer solution, pH 6.5

0.2% (w/v) n-dodecyl-β-D-maltoside (manufactured by Dojindo Laboratories)

0.067 U/ml peroxidase PEO-301 (Toyobo Co., Ltd.)

0.023 mM 10-(carboxymethylaminocarbonyl)-3,7-bis(dimethylamino)phenothiazine sodium (DA-67, manufactured by Wako Pure Chemical Industries, Ltd.)

HbA1c is measured according to the following procedures using Bio Majesty JCA-BM1650 (manufactured by JEOL Ltd.). 8 µl of ion-exchange water is added to 96 µl of the first reagent-A, and the mixture is incubated at 37° C. for 5 minutes. Then, 24 µl of the hydrogen peroxide sample having a known concentration is added thereto, and the quantitative reaction of hydrogen peroxide is allowed to progress at 37° C. for 5 minutes. The absorbance ($A_{694}$ and $A_{751}$) of the reaction solution for light at wavelengths of 694 nm and 751 nm is measured over time for 10 minutes after the mixing of the ion-exchange water with the first reagent-A to determine $A_{694/751}$ which is a difference therebetween. The concentration of the hydrogen peroxide is plotted on the abscissa against $A_{694/751}$ 10 minutes after the mixing of the ion-exchange water with the first reagent on the ordinate to prepare a calibration curve representing the correlation between the hydrogen peroxide concentration and $A_{694/751}$.

Next, the same measurement as above is performed using a hydrogen peroxide sample of unknown concentration instead of the hydrogen peroxide sample having a known concentration. The hydrogen peroxide concentration of the sample is determined using $A_{694/751}$ 10 minutes after the mixing of the ion-exchange water with the first reagent-A, and the calibration curve prepared above.

EXAMPLES

The present invention will be described more specifically with reference to the Examples given below. However, the present invention is not limited by these examples. Unless specified otherwise, commercially available products were used as the reagents.

[Example 1] Measurement of Absorbance when Hydrogen Peroxide Detection Reaction Mediated by Peroxidase was Completed In this Example the amount of change in absorbance was determined when hydrogen peroxide detection reaction was completed using an excess of peroxidase.

A reagent for hydrogen peroxide measurement having the following composition (formulation) was prepared, and the measurement of hydrogen peroxide was carried out using Bio Majesty JCA-BM1650 (manufactured by JEOL Ltd.).
(Sample)
100 mM MOPS-NaOH buffer solution, pH 6.5
0.00012% (w/v) hydrogen peroxide
(First Reagent-A)
30 mM MOPS-NaOH buffer solution, pH 6.5
0.2% (w/v) n-dodecyl-β-D-maltoside (manufactured by Dojindo Laboratories)
0.067 U/ml peroxidase PEO-301 (Toyobo Co., Ltd.)
0.023 mM 10-(carboxymethylaminocarbonyl)-3,7-bis(dimethylamino)phenothiazine sodium (DA-67, manufactured by Wako Pure Chemical Industries, Ltd.)
(Second Reagent)
0.48% (w/v) of the compound of Comparative Example 2 (Wako Pure Chemical Industries, Ltd.), any one compound of the present invention (all from Tokyo Chemical Industry Co., Ltd.), or compound-free (Comparative Example 1) ion-exchange water as shown in Table 1

8 µl of the second reagent was added to 96 µl of the first reagent-A, and the mixture was incubated at 37° C. for 5 minutes. Then, 24 µl of the sample was added thereto, and the quantitative reaction of hydrogen peroxide was allowed to progress at 37° C. for 5 minutes. The absorbance ($A_{694}$ and $A_{751}$) of the reaction solution for light at wavelengths of 694 nm and 751 nm was measured over time for 10 minutes after the mixing of the second reagent with the first reagent-A to determine the value of subtraction of $A_{751}$ from $A_{694}$, i.e., the value of $A_{694/751}$. Subsequently, ΔA was calculated by subtracting, from $A_{694/751}$, the value of (104/128) times $A_{694/751}$ 4.8 minutes after the mixing of the second reagent with the first reagent-A. Incidentally, 4.8 minutes after the mixing of the second reagent with the first reagent-A represents the time immediately before the addition of the sample. ΔA 9 minutes and 10 minutes after the mixing of the second reagent with the first reagent-A ($ΔA_{9\ min}$ and $ΔA_{10\ min}$) is shown in Table 1. As an example, the relationship between $A_{694/751}$ and $ΔA_{9\ min}$ and $ΔA_{10\ min}$ for Comparative Example 1 is shown in FIG. 1.

TABLE 1

|  | $ΔA_{9\ min}$ | $ΔA_{10\ min}$ |
|---|---|---|
| Not added (Comparative Example 1) | 0.079 | 0.079 |

TABLE 1-continued

|  | $ΔA_{9\ min}$ | $ΔA_{10\ min}$ |
|---|---|---|
| Tartrazine (Comparative Example 2) | 0.344 | 0.344 |
| Alizarin Yellow GG (Present invention 1) | 0.170 | 0.170 |
| Chrome Yellow (Present invention 2) | 0.272 | 0.272 |
| Direct Yellow 44 (Present invention 3) | 0.228 | 0.228 |
| 4-(Phenylazo)phenol (Present invention 4) | 0.122 | 0.122 |
| 2-Hydroxy-1-(2-hydroxy-4-sulfo-1-naphthylazo)-3-naphthoic Acid(Present invention 5) | 0.084 | 0.085 |

As shown in Table 1, no difference between $ΔA_{9\ min}$ and $ΔA_{10\ min}$ was observed for the compounds of the present invention and Comparative Examples. In other words, it can be understood that the quantitative reaction of hydrogen peroxide was completed in 10 minutes after the mixing of the second reagent with the first reagent-A. Accordingly, $ΔA_{10\ min}$ in each Comparative Example or the present invention was defined as ΔA when 100% of the quantitative reaction of hydrogen peroxide progressed under each condition ($ΔA_{100}$%).

[Example 2] Confirming the Effect of Accelerating Hydrogen Peroxide Detection Reaction Mediated by Peroxidase by the Compound of Present Invention Next, in this Example, the degree of acceleration of hydrogen peroxide detection reaction by the compound of the present invention was determined using a small amount of peroxidase.

A reagent for Hydrogen peroxide measurement having the following composition was prepared, and the measurement of hydrogen peroxide was carried out using Bio Majesty JCA-BM1650 (manufactured by JEOL Ltd.).
(Sample)
100 mM MOPS-NaOH buffer solution, pH 6.5
0.00012% (w/v) hydrogen peroxide
(First Reagent-B)
30 mM MOPS-NaOH buffer solution, pH 6.5
0.2% (w/v) n-dodecyl-β-D-maltoside (manufactured by Dojindo Laboratories)
0.013 U/ml peroxidase PEO-301 (Toyobo Co., Ltd.)
0.023 mM 10-(carboxymethylaminocarbonyl)-3,7-bis(dimethylamino)phenothiazine sodium (DA-67, manufactured by Wako Pure Chemical Industries, Ltd.)
(Second Reagent)
0.48% (w/v) of the compound of Comparative Example 2, any one compound of the present invention, or compound-free (Comparative Example 1) ion-exchange water as shown in Table 2

8 µl of the second reagent was added to 96 µl of the first reagent-B, and the mixture was incubated at 37° C. for 5 minutes. Then, 24 µl of the sample was added thereto, and the quantitative reaction of hydrogen peroxide was allowed to progress at 37° C. for 5 minutes. The absorbance ($A_{694}$ and $A_{751}$) of the reaction solution for light at wavelengths of 694 nm and 751 nm was measured over time for 10 minutes after the mixing of the second reagent with the first reagent-B to determine the value of subtraction of $A_{751}$ from $A_{694}$, i.e., the value of $A_{694/751}$. Subsequently, ΔA was calculated by subtracting, from $A_{694/751}$, the value of (104/128) times $A_{694/751}$ 4.8 minutes after the mixing of the second reagent with the first reagent-B. Incidentally, 4.8 minutes after the mixing of the second reagent with the first reagent-B represents the time immediately before the addition of the sample.

Next, ΔA calculated in this Example was divided by $\Delta A_{100}\%$ defined in Example 1 to calculate the degree of progression of hydrogen peroxide detection reaction. The degree of progression of hydrogen peroxide detection reaction 7.5 and 10 minutes after the mixing of the second reagent with the first reagent-B (in other words, 2.5 and 5 minutes, respectively, after the addition of the sample) is shown in Table 2.

TABLE 2

|  | Degree of progression of reaction (%) after 7.5 minutes | Degree of progression of reaction (%) after 10 minutes |
| --- | --- | --- |
| Not added (Comparative Example 1) | 55 | 83 |
| Tartrazine (Comparative Example 2) | 57 | 85 |
| Alizarin Yellow GG (Present invention 1) | 64 | 89 |
| Chrome Yellow (Present invention 2) | 66 | 92 |
| Direct Yellow 44 (Present invention 3) | 64 | 89 |
| 4-(Phenylazo)phenol (Present invention 4) | 69 | 90 |
| 2-Hydroxy-1-(2-hydroxy-4-sulfo-1-naphthylazo)-3-naphthoic Acid (Present invention 5) | 61 | 90 |

As shown in Table 2, Tartrazine, Alizarin Yellow GG, Chrome Yellow, Direct Yellow 44, 4-(phenylazo)phenol, and 2-hydroxy-1-(2-hydroxy-4-sulfo-1-naphthylazo)-3-naphthoic acid accelerated hydrogen peroxide detection reaction using peroxidase.

INDUSTRIAL APPLICABILITY

By using the peroxidase reaction accelerating agent of the present invention the amount of peroxidase formulated into a hydrogen peroxide measurement reagent can be reduced. Furthermore, by using the peroxidase reaction accelerating agent of the present invention, measurement sensitivity can be enhanced when the same amount of peroxidase is used.

All publications, patents and patent applications cited herein are incorporated herein by reference in their entirety.

The invention claimed is:
1. A method for measuring hydrogen peroxide, comprising the step of using peroxidase and a peroxidase reaction accelerating agent,
wherein the peroxidase reaction accelerating agent is represented by any of the following formulae:

[Formula 6]

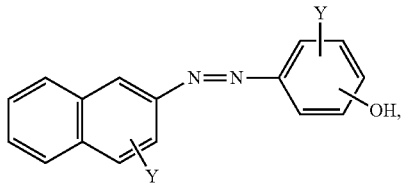

-continued

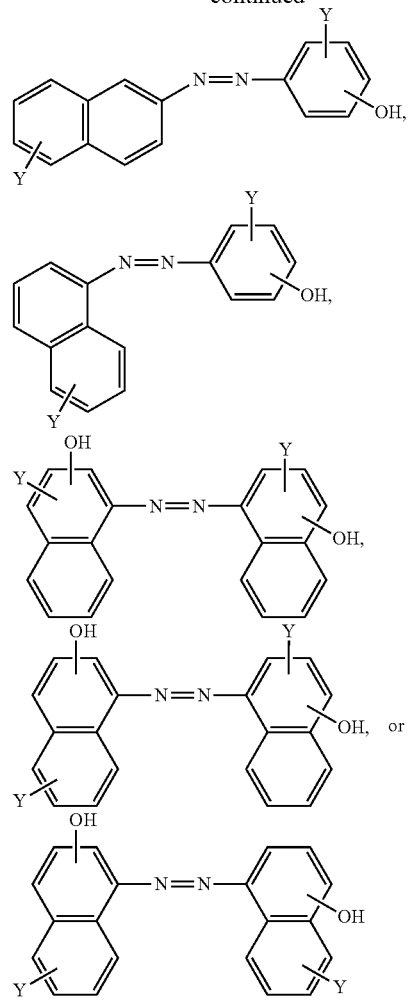

wherein
each X is independently selected from the group consisting of —H, —Na, —K, and —Li; and
each Y is independently selected from the group consisting of —H, —SO$_3$X, and —COOX, or,
wherein the peroxidase reaction accelerating agent is represented by the following formula:

[Formula 7]

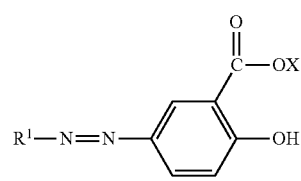

(III)

wherein
R$^1$ is a benzene ring or a naphthalene ring which may optionally be substituted with one or more substituents, wherein
the substituent(s) is selected from the group consisting of —SO$_3$X, and

[Formula 8]

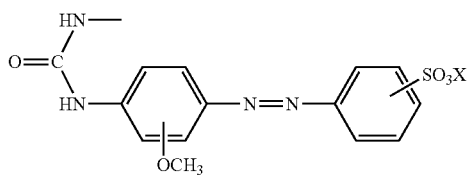

and

X is selected from the group consisting of —H, —Na, —K, and —Li.

2. The method according to claim 1, wherein the peroxidase reaction accelerating agent is represented by any of the following formulae:

[Formula 6]

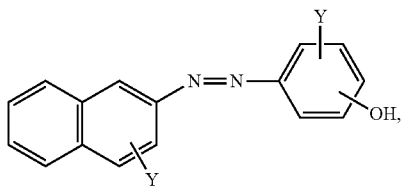

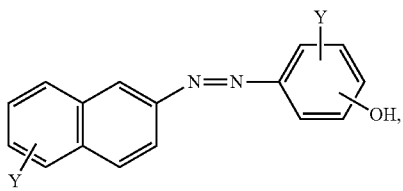

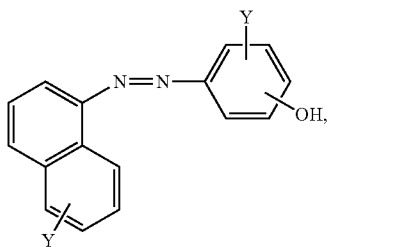

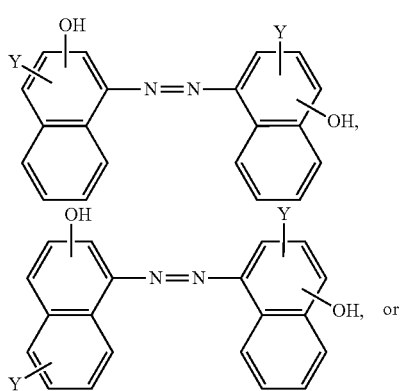

-continued

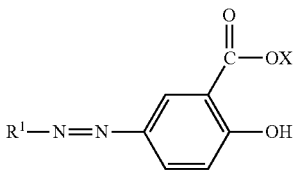

wherein each X is independently selected from the group consisting of —H, —Na, —K, and —Li; and each Y is independently selected from the group consisting of —H, —SO₃X, and —COOX.

3. The method according to claim 1, wherein the peroxidase reaction accelerating agent is represented by the following formula:

[Formula 7]

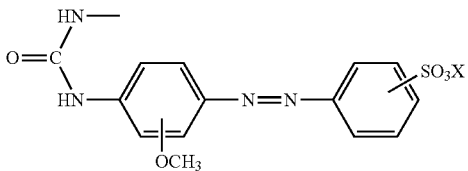
(III)

wherein

R¹ is a benzene ring or a naphthalene ring which may optionally be substituted with one or more substituents, wherein the substituent(s) is selected from the group consisting of SO₃X, and

[Formula 8]

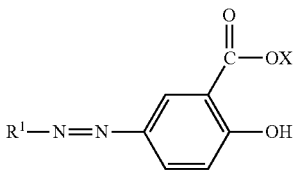

and

X is selected from the group consisting of —H, —Na, —K, and —Li.

4. The method according to claim 1, wherein the compound is a compound selected from the group consisting of a compound represented by the following formula (4-(phenylazo)phenol, CAS 1689-82-3):

[Formula 9]

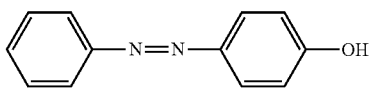
IV a compound represented by the following formula:

[Formula 10]

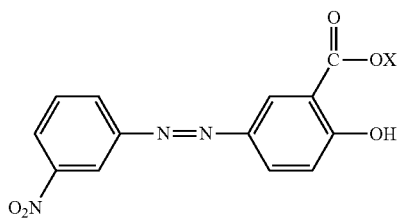

V wherein X is selected from the group consisting of —H, —Na, —K, and —Li, a compound represented by the following formula:

[Formula 11]

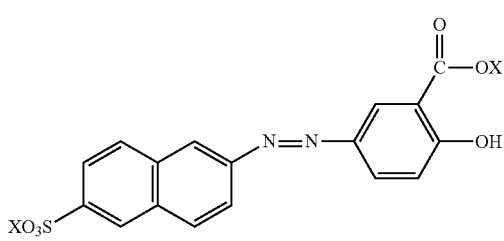

VI wherein each X is independently selected from the group consisting of —H, —Na, —K, and —Li, a compound represented by the following formula:

[Formula 12]

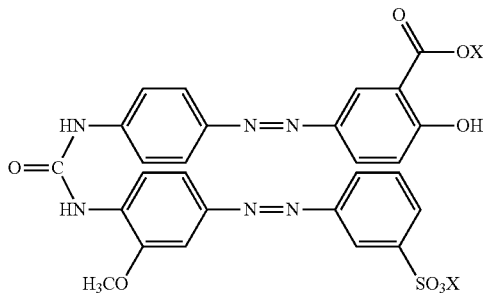

VII wherein each X is independently selected from the group consisting of —H, —Na, —K, and —Li,
and
a compound represented by the following formula:

[Formula 13]

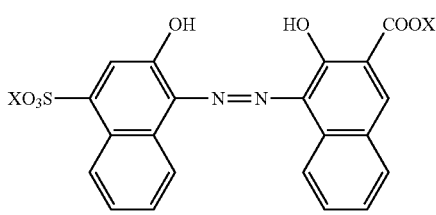

VIII wherein each X is independently selected from the group consisting of —H, —Na, —K, and —Li.

* * * * *